United States Patent
Rayner-Brandes et al.

(10) Patent No.: US 9,988,600 B2
(45) Date of Patent: Jun. 5, 2018

(54) CELL CULTURE MEDIA

(71) Applicant: MERCK PATENT GMBH, Darmstadt (DE)

(72) Inventors: Michael Howard Rayner-Brandes, Seeheim-Jugenheim (DE); Joerg Von Hagen, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days. days.

(21) Appl. No.: 14/904,294

(22) PCT Filed: Jun. 16, 2014

(86) PCT No.: PCT/EP2014/001635
§ 371 (c)(1),
(2) Date: Jan. 11, 2016

(87) PCT Pub. No.: WO2015/003773
PCT Pub. Date: Jan. 15, 2015

(65) Prior Publication Data
US 2016/0145565 A1    May 26, 2016

(30) Foreign Application Priority Data
Jul. 11, 2013   (EP) ..................... 13003514

(51) Int. Cl.
*C12N 5/02*    (2006.01)
*C12N 1/00*    (2006.01)
*C12N 5/00*    (2006.01)

(52) U.S. Cl.
CPC ........ *C12N 5/0018* (2013.01); *C12N 2500/50* (2013.01)

(58) Field of Classification Search
CPC combination set(s) only.
See application file for complete search history.

(56) References Cited

U.S. PATENT DOCUMENTS

| | | | |
|---|---|---|---|
| 3,579,465 A | 5/1971 | Schmolka et al. | |
| 3,740,421 A | 6/1973 | Schmolka et al. | |
| 3,925,241 A | 12/1975 | Schmolka et al. | |
| 4,416,898 A * | 11/1983 | Le Fur | A61K 31/195 514/562 |
| 4,490,403 A | 12/1984 | Pisecky et al. | |
| 6,383,810 B2 | 5/2002 | Fike et al. | |
| 7,572,632 B2 | 8/2009 | Fike et al. | |
| 2001/0049141 A1 | 12/2001 | Fike et al. | |
| 2004/0087022 A1 | 5/2004 | Fike et al. | |
| 2010/0317104 A1 | 12/2010 | Elefanty | |
| 2012/0276630 A1 | 11/2012 | Fike et al. | |
| 2013/0065300 A1 | 3/2013 | Fike et al. | |

FOREIGN PATENT DOCUMENTS

| | | | | |
|---|---|---|---|---|
| WO | 9836051 A1 | 8/1998 | | |
| WO | WO2013/096858 | * | 6/2013 | ............... C12N 5/00 |

OTHER PUBLICATIONS

Sakai K; "Use of nonionic surfactants for effective supply of phosphatidic acid in serum-free culture of Chinese hamster ovary cells" Journal of Bioscience and Bioengineering vol. 92, Issue 3, 2001, pp. 256-261.
Search report in corresponding EP application No. 14731911.5 dated May 10, 2017.
Hossler P; "Improvement of mammalian cell culture performance through surfactant enabled concentrated feed media." Biotechnol Prog. Jul.-Aug. 2013;29(4):1023-33. doi: 10.1002/btpr.1739. Epub May 11, 2013.
International Search Report for PCT/EP2014/001635 dated Sep. 30, 2014.
Walowtiz, J. L. et al., "Efficient Lipid Delivery to Hybridoma Culture by use of cyclodextrin in a novel granulated dey-form medium technology," Biotechnology Progress, American Institute of Chemical Engineers, Jan. 1, 2003, vol. 19, No. 1, pp. 64-68.
Budkina, O. A. et al., "Cytotoxicity of nonionic amphiphilic copolymers," Polymer Science Series A., Sep. 1, 2012, vol. 54, No. 9, pp. 707-717.

* cited by examiner

*Primary Examiner* — Allison M Fox
(74) *Attorney, Agent, or Firm* — Millen, White, Zelano, Branigan, P.C.

(57) ABSTRACT

The present invention relates to cell culture media comprising polymer embedded components. Some components show poor stability in dry powder cell culture media. Others are hygroscopic. Such components can be embedded into polymers to increase stability and reduce clumping.

22 Claims, 2 Drawing Sheets

CELL CULTURE MEDIA

The present invention relates to dry cell culture media comprising polymer embedded components. Some components show poor stability in dry powder cell culture media, whereas others are hygroscopic. Some components take an extensive time to dissolve completely. Such components can be embedded into polymers to increase stability and reduce clumping.

Cell culture media in aqueous solution can provide an environment which supports and maintains the growth of cells and/or maintains a desired physiological cellular condition adventitious to the targeted production of certain products.

Cell culture media comprise of a complex mixture of components, sometimes more than one hundred different components, depending on the type of organism whose growth and/or targeted physiological status shall be supported.

The cell culture media required for the propagation of mammalian, insect or plant cells are typically much more complex than the media to support the growth of bacteria, yeast or fungi.

The first cell culture media that were developed were complex media consisting of diverse mixtures of components which were very poorly chemically defined, poorly characterized and difficult to manufacture with a consistent quality, such as plasma, serum, embryo extracts, and/or other biological extracts or peptones. A major advance was thus made with the development of chemically defined media. Chemically defined media often comprise of but are not exclusively limited to amino acids, vitamins, sugars, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. These are manufactured for the purpose of dissolving in water and/or aqueous solutions and in the dissolved state are designed, often with other supplements, for supplying cells with a substantial nutrient base for growth and/or production of biopharmaceuticals from said cells and/or used as a feed to supply cells when specific nutrients become limiting.

A limiting factor for the preparation and the use of cell culture media from dry powder is the poor stability of some components, which tend to degrade and/or or oxidize during storage of the dry powder medium. Some components are hygroscopic which often results in clumping of the medium leading to stability and/or other quality problems restricting their industrial application(s). In addition the water attracted by the hygroscopic compounds might lead to increased microbial growth as well as degradation of neighbouring components.

Consequently it would be favourable to find a way to improve the stability of sensitive media components and reduce the negative influence of hygroscopic components.

It has been found that sensitive and/or hygroscopic media components can be stabilized by embedding them in a polymer matrix. The attraction of water by hygroscopic components is reduced and components sensitive to oxidation or degradation show increased stability by imbedding them in and/or coating them and/or contacting them with other components which increase said components stability whether the instability and/or decrease in quality be induced by oxidation and/or hygroscopicity and/or agglomeration due to van de waals and/or electrostatic forces, thus reducing also the effect such oxidised and/or wet/damp/sticky components can have on neighboring components.

The present invention is therefore directed to a dry powder cell culture medium comprising at least one polymer embedded component.

In a preferred embodiment, the polymer is a poloxamer.

In another preferred embodiment the component is L-glutamine, sodium hydrogen carbonate, calcium chloride×2 $H_2O$, cholin chloride, ferric nitrate×9 $H_2O$, ferrous sulphate×7 $H_2O$, sodium phosphate or monosodium phosphate ($NaH_2PO_4$) monohydrate.

In one embodiment, the cell culture medium comprises two or more polymer embedded components.

In one embodiment, the polymer embedded components have been prepared by hot melt extrusion.

In another embodiment the polymer embedded components have been prepared by wet granulation.

In one embodiment the cell culture medium is a mammalian cell culture medium.

In another embodiment, the cell culture medium is a chemically defined cell culture medium.

The present invention is further directed to a method for producing a cell culture medium according to the present invention by
a) Providing one or more polymer embedded components
b) Providing the other components of the cell culture medium, mixing them and subjecting them to milling
c) Adding the polymer embedded components of step a) to the milled mixture resulting from step b)

In a preferred embodiment step b) is performed in a ball mill, pin mill, fitz mill or a jet mill, most preferred in a pin mill, fitz mill or a jet mill.

In another preferred embodiment, the mixture from step a) is cooled to a temperature below 0° C. prior to milling.

The present invention is further directed to a process for culturing cells by
a) providing a bioreactor
b) dissolving the cell culture medium according to the present invention in water or an aqueous buffer and mixing the cells to be cultured with it
c) incubating the mixture of step b).

Figure 1:
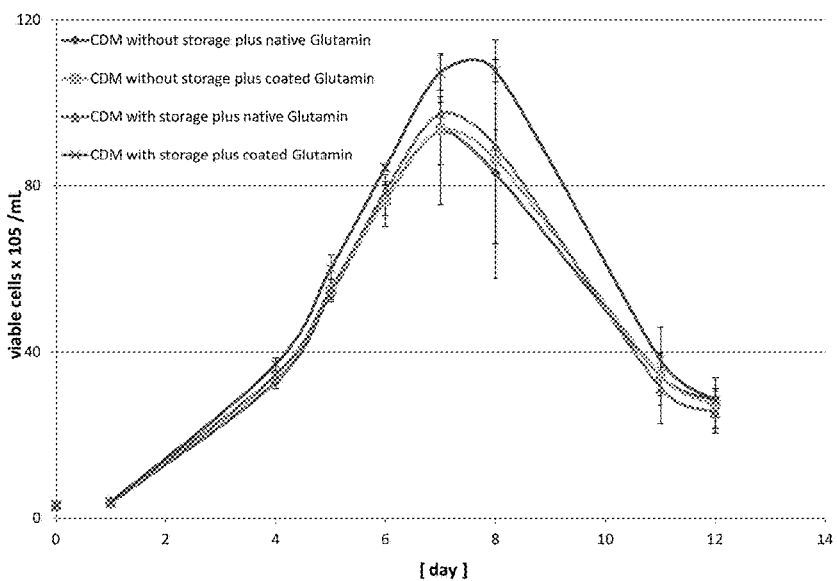
FIGS. 1 and 2 show the CHO S performance testing. Further details can be found in Example 2.

A cell culture medium according to the present invention is any mixture of components which maintains and/or supports the in vitro growth of cells and/or supports a particular physiological state. It might be a complex medium or a chemically defined medium. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells as well as media supplements or feeds. In a preferred embodiment the cell culture medium is a full medium or a medium which lacks few components.

Typically, the cell culture media according to the invention are used to maintain and/or support the growth of cells and/or supports a particular physiological state in a bioreactor.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute chemically poorly defined proteins and/or peptides and/or hydrolysates to the media. Chemically undefined or poorly defined chemical components are those whose chemical composition and structure is not well known, are present in poorly defined and varying composition or could only be defined with enormous experimental effort—comparable to the evaluation of the chemical composition and structure of a protein like albumin or casein.

A powdered cell culture medium or a dry powder medium is a cell culture medium typically resulting from a milling process or a lyophilisation process. That means the powdered cell culture medium is a granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

Cells to be cultured with the media according to the present invention may be prokaryotic cells like bacterial cells or eukaryotic cells like yeast, fungi, plant or animal cells. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

The size of a particle means the mean diameter of the particle. The particle diameter is determined by laser light scattering in silicone oil.

An inert atmosphere is generated by filling the respective container or apparatus with an inert gas. Suitable inert gases are noble gases like argon or preferably nitrogen. These inert gases are minimally-reactive and prevent undesirable chemical reactions from taking place. In the process according to the present invention, generating an inert atmosphere means that the concentration of oxygen is reduced below 10% (v/v) absolute, e.g. by introducing liquid nitrogen or nitrogen gas.

Different types of mills are known to a person skilled in the art.

A pin mill, also called centrifugal impact mill, pulverizes solids whereby protruding pins on high-speed rotating disks provide the breaking energy. Pin mills are for example sold by Munson Machinery (USA), Premium Pulman (India) or Sturtevant (USA).

A jet mill uses compressed gas to accelerate the particles, causing them to impact against each other in the process chamber. Jet mills are e.g. sold by Sturtevant (USA) or PMT (Austria).

A fitz mill commercialized by Fitzpatrick (USA), uses a rotor with blades for milling.

A process that is run continuously is a process that is not run batchwise. If a milling process is run continuously it means that the media ingredients are permanently and steadily fed into the mill over a certain time.

The cell culture media according to the present invention typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, digests or extracts, fatty acids and/or fatty acid derivatives and/or pluronic product components (block copolymers based on ethylene oxide and propylene oxide) in particular Poloxamer 188 sometimes called Pluronic F 68 or Kolliphor P 188 or Lutrol F 68 and/or surface active components like chemically prepared non-ionic surfactants. One example of a suitable non-ionic surfactant are difunctional block copolymer surfactants terminating in primary hydroxyl groups also called poloxamers, e.g. available under the trade name Pluronic® from BASF, Germany.

Saccharide components are all mono- or di-saccharides, like glucose, galactose, ribose or fructose (examples of monosaccharides) or sucrose, lactose or maltose (examples of disaccharides). Saccharide components may also be oligo- or polysaccharides.

Examples of amino acids according to the invention are tyrosine, the proteinogenic amino acids, especially the essential amino acids, leucine, isoleucine, lysine, methionine, phenylalanine, threonine, tryptophane and valine, as well as the non-proteinogenic amino acids like D-amino acids.

Tyrosine means L- or D-tyrosine, preferably L-tyrosine.
Cysteine means L- or D-cysteine, preferably L-cysteine.
Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors and analogues are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are copper(II) sulphate pentahydrate ($CuSO_4 \cdot 5H_2O$), sodium chloride (NaCl), calcium chloride ($CaCl_2 \cdot 2H_2O$), potassium chloride (KCl), Iron(II)sulphate, sodium phosphate monobasic anhydrous ($NaH_2PO_4$), magnesium sulphate anhydrous ($MgSO_4$), sodium phosphate dibasic anhydrous ($Na_2HPO_4$), magnesium chloride hexahydrate ($MgCl_2 \cdot 6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, vitamin B12, flavin mononucleotide and derivatives, glutathione, heme, nucleotide phosphates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

Freezing according to the present invention means cooling to a temperature below 0° C.

The gist of the present invention is to provide powdered cell culture media that are stable for storage and can be easily processed without clumping or degradation of components. When the dry powder media are dissolved in a suitable solvent by admixing the powder and the solvent, the powder dissolves and produces a liquid cell culture medium such as a full medium, a medium supplement, a medium subgroup or a feed with a desired and homogenous concentration of the media components.

In principle, all cell culture media components can be embedded in polymers. Typically, components which are sensitive to degradation or oxidation or other chemical modification, components whose solubility shall be improved and/or hygroscopic components are embedded in polymers. Examples of such media components are L-glutamine, sodium hydrogen carbonate, calcium chloride×2 $H_2O$, choline chloride, ferric nitrate×9 $H_2O$, ferrous sulphate×7 $H_2O$, sodium phosphate or monosodium phosphate ($NaH_2PO_4$) monohydrate.

Table 1 shows a list of components of DMEM F12 medium. For all components the effect of polymer embedding is shown.

In Table 1, "Solu" means that if the component is embedded according to the present invention and used in the media composition in its embedded form, the solubility of said component is improved compared to the non-embedded form.

In Table 1, "Stab" means that if the component is embedded according to the present invention and used in the media composition in its embedded form, the stability of said component is improved compared to the non-embedded form.

In Table 1, "Oxid" means that if the component is embedded according to the present invention and used in the media composition in its embedded form, the stability against oxidation of said component is improved compared to the non-embedded form.

In Table 1, "Hygros" means that if the component is embedded according to the present invention and used in the media composition in its embedded form, the ability of said substance to attract and hold water molecules from the surrounding environment is reduced compared to the non-embedded form. In other words, the embedded component is less hygroscopic.

In Table 1, "NA" means "not applicable". That means for components for which the table says NA the embedding according to the present invention does not lead to any obvious effect.

Embedded in polymers means that the components are partially or fully coated by a polymer or dispersed in a polymer matrix. The components might be dispersed in the polymer matrix as particles or at a molecular level, thus forming solid solutions.

Suitable polymers for embedding components according to the present invention are water soluble polymers.

Examples of suitable polymers are soluble cellulose derivatives such as ethyl cellulose, hydroxypropyl methylcellulose, hydroxypropylcellulose, methylcellulose, carboxymethylcellulose, hydroxymethylcellulose, hydroxyethylcellulose; poly(vinyl alcohol), partially hydrolyzed polyvinyl alcohol, cellulose acetate, hydroxypropyl methylcellulose phthalate, cellulose acetate phthalate, cellulose acetate trimellitate, polyethylene-polypropylene glycol (e.g. Poloxamer™), carbomer, polycarbophil, chitosan; natural gums such as gum guar, gum acacia, gum tragacanth, or gum xanthan, and povidone; waxes such as polyethylene glycol; or methacrylic acid polymers such as Eudragit® RL and Eudragit® RS; or polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

In a preferred embodiment, the polymer is a polyethylene glycol (PEG)/polypropylene glycol (PPG) block copolymer, a polyvinylpyrrolidon or a polyvinyl caprolactam-polyvinyl acetat-polyethylene glycol graft copolymer Polyethylene glycol (PEG)/polypropylene glycol (PPG) block copolymers are also called poloxamers. The poloxamers, CAS number 9003-11-6, to be preferably used as polymer according to the present invention have the general formula I

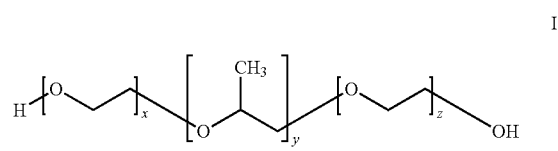

with x and z preferably independently being 2 to 130 and y preferably being 15 to 67.

They are commercially available (Pluronics® or Lutrole®, e.g., a Pluronic® solution, gel, or solid, such as Pluronic® F-127). Alternatively, the poloxamer can be made from raw materials according to methods known in the art (see, for example, U.S. Pat. Nos. 3,579,465 and 3,740,421).

Further information about poloxamers can be found in Hagers Handbuch der Pharmazeutischen Praxis, volume 9 "Stoffe P-Z", 1994, pages 282 to 284.

Polyvinylpyrrolidone polymers are commercially available as Kollidon® from BASF, Germany.

Polyvinyl caprolactam-polyvinyl acetat-polyethylene glycol graft copolymers are commercially available as Soluplus® from BASF, Germany.

The embedding of the media components in the polymer might be done by several methods.

If the polymer shall be applied in form of a coating, the coating may be performed by applying film-forming polymer(s), with or without additional ingredients such a stabilizers, as a solution/suspension using any conventional coating technique known in the art such as spray coating in a conventional coating pan or fluidized bed processor, dip coating, or compression coating.

In a preferred embodiment, the media components are dispersed in a matrix formed by the polymer.

Such a dispersion can be made by procedures like hot melt extrusion, spray drying, solid dispersion, fluidized bed granulation, solid dispersion or co-lyophilisation.

Extrusion can be simply defined as the process of forming a new material (the extrudate) by forcing it through an orifice or die under controlled conditions, such as temperature, mixing, feed-rate and pressure. In hot melt extrusion, the polymer is in the molten state. After extrusion, the hot melt extrudate is a solid that comprises the polymer and the dispersed media component.

If the components are embedded in the polymer by hot meld extrusion, the polymers should have a melting point below 200° C. Preferably, the polymers have a melting point below 150° C., most preferred below 75° C.

It was found that the hot melt extrusion (HME) approach can suitably be applied when using a poloxamer like Poloxamer 188 (Lutrol F68) as a polymer.

For co-lyophilisation, in a first step, all components to be co-lyophilised are dissolved in a solvent.

The components can be solubilised in one solvent. Alternatively, each component can be dissolved in a separate solvent and the resulting two or more solutions of different components can then be mixed. Typically, all solutions to be mixed have the same solvent.

Suitable solvents are those in which all components are soluble. Examples of suitable solvents are organic solvent or water or mixtures thereof. Preferred is water.

Once the solvent is chosen and the components have been dissolved, the resulting mixture is frozen and lyophilized to dryness. Sometimes an additional solvent is added to the mixture to facilitate lyophilisation. Typically lyophilisation is performed at a temperature below −20° C., preferably at around −80° C. The liquid is typically removed by applying reduced pressure.

For spray drying the media component and the polymer are dissolved in a solvent. Examples of suitable solvents are organic solvent or water or mixtures thereof. Preferred is water. The solution is then placed into a spray-drying apparatus so that the solution is converted into its corresponding powder by spraying the solution into a chamber in the apparatus under appropriate conditions to produce the powder, such as under controlled temperature and humidity, until the powder is formed.

In a typical spray-drying approach, the solution is aspirated into the apparatus and is atomized into a spray with a rotary- or nozzle-type atomizer. The resulting atomized liquid spray is then mixed with a gas (e.g., nitrogen or more preferably air) and sprayed into a drying chamber under conditions sufficient to promote production of a powdered product.

For solid dispersion, the media component and the polymer are mixed and heated so that at least the polymer melts. After thorough mixing the mixture is cooled again to give a solid comprising the polymer and the media component.

The solid obtained after hot melt extrusion, lyophilisation, spray drying, solid dispersion, fluidized bed granulation or other embedding procedures is then preferably milled, e.g. in a ball mill, to generate particles of homogenous size. The resulting particles comprising the at least one media component embedded in a polymer typically have a particle size below 200 μm. Preferred are particle sizes below 100 μm. Favourable particle sizes are between 15 μm and 100 μm.

It is understood that the polymer embedded component may be a single type of component or a mixture of two or more components. It is further understood that the polymer of the polymer embedded component might be a single type of polymer or a mixture of two or more polymers. In a preferred embodiment, each polymer embedded component contains only one media component and one polymer. The polymer embedded component might additionally comprise stabilizers or plasticisers but in a preferred embodiment the polymer embedded component contains only the media component and the polymer.

Typically the polymer embedded components comprise between 0.01 and 99% by weight of the media component and between 99.99 and 1% by weight of the polymer. Preferably they comprise between 10 and 90% by weight of the media component and between 90 and 10% by weight of the polymer.

The powdered cell culture media of the present invention are preferably produced by mixing all components beside the polymer embedded components and milling them. The mixing of the components is known to a person skilled in the art of producing dry powdered cell culture media by milling. Preferably, all components are thoroughly mixed prior to milling so that all parts of the mixture have nearly the same composition. The higher the uniformity of the composition, the better the quality of the resulting medium with respect to homogenous cell growth. The polymer embedded components are preferably added to the mixture after milling, especially when the polymer embedded components is a coated components. If the component is dispersed in a polymer matrix it may also be mixed with the other components prior to milling and subjected to milling with them.

The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills.

A large scale equipment mill with a disc diameter of about 40 cm is e.g. typically run at 1-6500 revolutions per minute in case of a pin mill, preferred are 1-3000 revolutions per minute.

The milling can be done under standard milling conditions resulting in powders with particle sizes between 10 and 300 μm, most preferably between 25 and 100 μm.

Preferably, all components of the mixture which is subjected to milling are dry. This means, if they comprise water, they do only comprise water of crystallization but not more than 10%, preferably not more than 5% most preferred not more than 2% by weight of unbound or uncoordinated water molecules.

In a preferred embodiment, the milling is performed in an inert atmosphere. Preferred inert protective gas is nitrogen.

In another preferred embodiment, all components of the mixture are frozen prior to milling. Freezing of the ingredients prior to the milling can be done by any means that ensures a cooling of the ingredients to a temperature below 0° C. and most preferably below −20° C. In a preferred embodiment the freezing is done with liquid nitrogen. This means the ingredients are treated with liquid nitrogen, for example by pouring liquid nitrogen into the container in which the ingredients are stored prior to introduction into the mill. In a preferred embodiment, the container is a feeder. If the container is a feeder the liquid nitrogen is preferably introduced at the side or close to the side of the feeder at which the ingredients are introduced.

Typically the ingredients are treated with the liquid nitrogen over 2 to 20 seconds.

Preferably the cooling of the ingredients is done in a way that all ingredients that enter into the mill are at a temperature below 0° C., most preferred below −20° C.

In a preferred embodiment, all ingredients are put in a container from which the mixture is transferred in a feeder, most preferred in a metering screw feeder. In the feeder the ingredients are sometimes further mixed—depending on the type of feeder—and additionally cooled. The frozen mixture is then transferred from the feeder to the mill so that the mixture which is milled in the mill preferably still has a temperature below 0° C., more preferred below −20° C.

Typically the blending time, that means the residence time of the mixture of ingredients in the feeder is more than one minute, preferably between 15 and 60 minutes.

A metering screw feeder, also called dosage snail, is typically run at a speed of 10 to 200 revolutions per minute, preferably it is run at 40 to 60 revolutions per minute.

Typically, the temperature of the mill is kept between −50 and +30° C. In a preferred embodiment, the temperature is kept around 10° C.

The oxygen level during milling preferably is below 10% (v/v).

The process can be run e.g. batch-wise or continuously. In a preferred embodiment the process according to the present invention is done continuously by, over a certain time, permanently filling the mixture of ingredients into a feeder for cooling and permanently filling cooled mixture from the feeder into the mill.

For use of the milled powdered media a solvent, preferably water (most particularly distilled and/or deionized water or purified water or water for injection) or an aqueous buffer is added to the media and the components are mixed until the medium is totally dissolved in the solvent.

The water or aqueous buffer may also comprise saline, soluble acid or base ions providing a suitable pH range (typically in the range between pH 1.0 and pH 10.0), stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

The present invention is further directed to a process for culturing cells by
a) providing a bioreactor
b) mixing the cells to be cultured with a cell culture medium according to the present invention that has been dissolved in water or an aqueous buffer
c) incubating the mixture of step b)

A bioreactor is any unit suitable for the culture of cells, like a container, vessel or tank in which cells can be cultured. A bioreactor is typically sterilized prior to use. Incubation is typically done under suitable conditions like suitable temperature etc. A person skilled in the art is aware of suitable incubation conditions for supporting or maintaining the growth/culturing of cells.

The cell culture media of the present invention comprising one or more polymer embedded components show better stability compared to standard media when they are stored.

In addition, the flow properties of the cell culture media of the present invention comprising one or more polymer embedded components are better than those of comparable standard media as the hygroscopic components are shielded.

The present invention is further illustrated by the following figures and examples, however, without being restricted thereto.

The entire disclosure of all applications, patents, and publications cited above and below and of corresponding EP application 13003514.0 filed Jul. 11, 2013, are hereby incorporated by reference.

TABLE 1

| No. | CAS-No. [5] | component | embedding effect |
|---|---|---|---|
| 1 | 56-40-6 | Glycine | Solu |
| 2 | 58-85-5 | Biotin | Stab |
| 3 | 10043-52-4 | Calcium chloride (anhydrous) | Hygros |
| 4 | 67-48-1 | Choline chloride | Hygros |
| 5 | 7758-99-8 | Copper sulfate 5H$_2$O | Solu |
| 6 | 137-08-6 | D-Calcium pantothenate | na |
| 7 | 7782-61-8 | Ferric nitrate 9H$_2$O | Solu |
| 8 | 7782-63-0 | Ferrous sulfate 7H$_2$O | Solu |

TABLE 1-continued

| No. | CAS-No. [5] | component | embedding effect |
|---|---|---|---|
| 9 | 59-30-3 | Folic acid | Stab |
| 10 | 68-94-0 | Hypoxanthine Na | na |
| 11 | 87-89-8 | i-Inositol | na |
| 12 | 56-41-7 | L-Alanine | Solu |
| 13 | 1119-34-2 | L-Arginine hydrochloride | Solu |
| 14 | 5794-13-8 | L-Asparagine H$_2$O | Solu |
| 15 | 56-84-8 | L-Aspartic acid | Solu |
| 16 | 7048-04-6 | L-Cysteine hydrochloride H$_2$O | Solu |
| 17 | 30925-07-6 | L-Cystine 2HCl (mikronisiert) aus 200635 | Solu |
| 18 | 56-86-0 | L-Glutamic acid | Solu |
| 19 | 56-85-9 | L-Glutamine | Stab |
| 20 | 5934-29-2 | L-Histidine HCl H$_2$O | Solu |
| 21 | 73-32-5 | L-Isoleucine | Solu |
| 22 | 61-90-5 | L-Leucine | Solu |
| 23 | 657-27-2 | L-Lysine hydrochloride | Solu |
| 24 | 63-68-3 | L-Methionine | Solu |
| 25 | 63-91-2 | L-Phenylalanine | Solu |
| 26 | 147-85-3 | L-Proline | Solu |
| 27 | 56-45-1 | L-Serine | Solu |
| 28 | 72-19-5 | L-Threonine | Solu |
| 29 | 73-22-3 | L-Thryptophan | Solu |
| 30 | 122666-87-9 | L-Tyrosine 2Na | Solu |
| 31 | 72-18-4 | L-Valine | Solu |
| 32 | 7791-18-6 | Magnesium chloride (hexahydrate) | na |
| 33 | 7487-88-9 | Magnesium sulfate (anhydrous) | Hygros |
| 34 | 98-92-0 | Niacinamide | Stab |
| 35 | 143-74-8 | Phenol red | na |
| 36 | 7447-40-7 | Potassium chloride | na |
| 37 | 333-93-7 | Putrescine 2HCl | Stab |
| 38 | 58-56-0 | Pyridoxine HCl | Stab |
| 39 | 83-88-5 | Riboflavin | Stab |
| 40 | 7647-14-5 | Sodium chloride | na |
| 41 | 7558-79-4 | Sodium Phosphate dibasic anhydrous | na |
| 42 | 10049-21-5 | Sodium Phosphate monobasic H$_2$O | na |
| 43 | 113-24-6 | Sodium pyruvate | Stab |
| 44 | 67-03-8 | Thiamine HCl | Stab |
| 45 | 50-89-5 | Thymidine | na |
| 46 | 68-19-9 | Vitamin B12 | Solu |
| 47 | 7446-20-0 | Zinc sulafte 7H$_2$O | Solu |
| 48 | 1077-28-7 | DL-alpha-lipoic acid | Oxid |
| 49 | 60-33-3 | Linoleic acid | Oxid |
| 50 | 50-99-7 | D-Glucose | na |

EXAMPLES

The following examples represent practical applications of the invention.

1. Preparation of Sodium Hydrogen Carbonate Embedded in Poloxamer

The poloxamer embedded sodium hydrogen carbonate is prepared by hot melt extrusion using a Unilab H00533 Hotmelt.

Educts:
2500 g of sodium hydrogen carbonate in form of particles between about 100 and 200 μm.
1000 g of poloxamer (BASF, Germany) in form of a melt as spraying liquid Specifications:
2 Hüttlin-3 component nozzles, 1.2 mm diameter
4×1 mm Teflon tubes
Spraying air flap: 2.3 mm
Microclimate: steady 40° C.
Tubes: 100° C.
Vessel: 130° C.
Spraying air: 130° C.

2. CHO S Performance Testing of Sodium Hydrogen Carbonate and L-Glutamine Embedded in Poloxamer The poloxamer embedded components are prepared according to the procedure of Example 1.

CHO S cells are seeded in Cellvento CHO 100 (EMD Millipore, US) with native and embedded sodium hydrogen carbonate and L-glutamine and stored over 4 weeks at 4° C.

Figure 2:
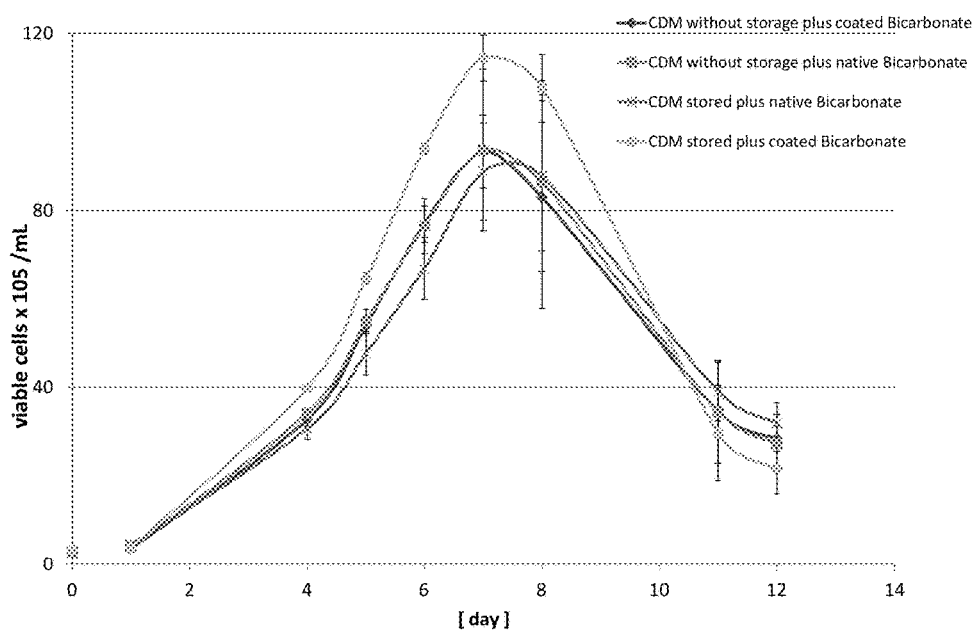

FIGS. 1 and 2 show the CHO S performance testing.

The invention claimed is:

1. A dry powder cell culture medium comprising at least one polymer embedded component, wherein said polymer is a poloxamer or a mixture thereof and said component is L-glutamine, sodium hydrogen carbonate, calcium chloride×2 H$_2$O, choline chloride, ferric nitrate×9 H$_2$O, ferrous sulphate×7 H$_2$O, sodium phosphate, or monosodium phosphate (NaH$_2$PO$_4$) monohydrate.

2. The cell culture medium according to claim 1, wherein said cell culture medium is a mammalian cell culture medium.

3. The cell culture medium according to claim 1, wherein said cell culture medium is a chemically defined cell culture medium.

4. The cell culture medium according to claim 1, wherein said polymer embedded component is prepared by hot melt extrusion.

5. The cell culture medium according to claim 1, wherein said polymer embedded component is prepared by wet granulation.

6. The cell culture medium according to claim 1, wherein said cell culture medium comprises two or more polymer embedded components.

7. The cell culture medium according to claim 6, wherein said polymer embedded components are prepared by hot melt extrusion.

8. The cell culture medium according to claim 6, wherein said polymer embedded components are prepared by wet granulation.

9. The cell culture medium according to claim 1, wherein said cell culture media comprises one or more saccharide components, one or more amino acids, one or more vitamins or vitamin precursors, one or more salts, one or more buffer components, one or more co-factors, and/or one or more nucleic acid components.

10. The cell culture medium according to claim 9, wherein
said one or more saccharide components are selected from glucose, galactose, ribose, fructose, sucrose, lactose and maltose,
said one or more amino acids are selected from tyrosine, leucine, isoleucine, lysine, methionine, phenylalanine, threonine, tryptophan and valine,
said one or more vitamins are selected from Vitamin A, Vitamin B1, Vitamin B2, Vitamin B3, Vitamin B5, Vitamin B6, Vitamin B7, Vitamin B9, Vitamin B12, Vitamin C, Vitamin D, Vitamin E and Vitamin K,
said one or more salts are selected from copper(II) sulphate pentahydrate, sodium chloride, calcium chloride, potassium chloride, iron(II)sulphate, sodium phosphate monobasic anhydrous, magnesium sulphate anhydrous, sodium phosphate dibasic anhydrous, magnesium chloride hexahydrate, and zinc sulphate heptahydrate, and
said one or more nucleic acid components are selected from cytosine, guanine, adenine, thymine, uracil, cytidine, uridine, adenosine, guanosine, thymidine, denosine monophosphate, adenosine diphosphate, and adenosine triphosphate.

11. The cell culture medium according to claim 1, wherein said polymer embedded component(s) comprise between 10 and 90% by weight of the component and between 90 and 10% by weight of said polymer.

12. The cell culture medium according to claim 1, wherein said polymer embedded component(s) have a particle size below 200 µm.

13. The cell culture medium according to claim 1, wherein said polymer embedded component(s) between 15 µm and 100 µm.

14. The cell culture medium according to claim 1, wherein said poloxamer is of the following formula:

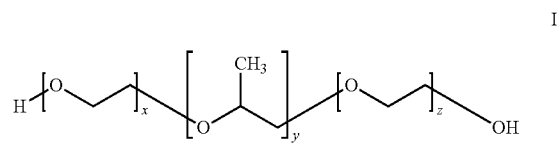

wherein x and z are each independently 2 to 130 and y is 15 to 67.

15. A method for producing a cell culture medium, said method comprising:
a) Providing a dry powder cell culture medium according to claim 1,
b) Providing other components of the cell culture medium, mixing said other components to form a mixture, and subjecting said mixture to milling to form a milled mixture,
c) mixing said dry powder cell culture medium with the milled mixture of b).

16. The method according to claim 15, wherein b) is performed in a ball mill, pin mill, fitz mill or a jet mill.

17. The method according to claim 15, wherein said mixture is cooled to a temperature below 0° C. prior to milling.

18. A method according to claim 15, wherein said other components are selected from saccharide components, amino acids, vitamins, vitamin precursors, salts, buffer components, co-factors, and nucleic acid components.

19. A method according to claim 15, wherein said other components are selected from saccharide components, amino acids, vitamins, vitamin precursors, salts, buffer components, co-factors, nucleic acid components, sodium pyruvate, insulin, vegetable proteins, fatty acids, fatty acid derivatives, and poloxamer components.

20. A process for culturing cells, said process comprising:
a) providing a bioreactor,
b) dissolving the cell culture medium according to claim 1 in water or an aqueous buffer,
c) mixing the cells to be cultured with the medium resulting from b), and
d) incubating the resultant mixture of c).

21. A process according to claim 20, wherein the cells to be cultured are prokaryotic cells.

22. A process according to claim 20, wherein the cells to be cultured are eukaryotic cells.

* * * * *